(12) United States Patent
Price

(10) Patent No.: US 9,603,812 B2
(45) Date of Patent: *Mar. 28, 2017

(54) TREATMENT OF AUTISTIC SPECTRUM DISORDER

(71) Applicant: Richard Louis Price, Suffern, NY (US)

(72) Inventor: Richard Louis Price, Suffern, NY (US)

(*) Notice: Subject to any disclaimer, the term of this patent is extended or adjusted under 35 U.S.C. 154(b) by 118 days.

This patent is subject to a terminal disclaimer.

(21) Appl. No.: 14/245,121

(22) Filed: Apr. 4, 2014

(65) Prior Publication Data

US 2014/0309271 A1    Oct. 16, 2014

Related U.S. Application Data

(63) Continuation-in-part of application No. 14/166,483, filed on Jan. 28, 2014, which is a continuation-in-part of application No. 13/860,824, filed on Apr. 11, 2013, now Pat. No. 9,211,284.

(51) Int. Cl.
| | |
|---|---|
| *A61K 31/047* | (2006.01) |
| *A61K 31/4168* | (2006.01) |
| *A61K 31/165* | (2006.01) |
| *A61K 45/06* | (2006.01) |

(52) U.S. Cl.
CPC .......... *A61K 31/047* (2013.01); *A61K 31/165* (2013.01); *A61K 31/4168* (2013.01); *A61K 45/06* (2013.01)

(58) Field of Classification Search
CPC ................ A61K 31/047; A61K 31/165; A61K 31/4168; A61K 45/06
See application file for complete search history.

(56) References Cited

U.S. PATENT DOCUMENTS

| | | |
|---|---|---|
| 3,454,701 A | 7/1969 | Zeile et al. |
| 5,854,290 A | 12/1998 | Arnsten et al. |
| 5,869,100 A | 2/1999 | Horacek |
| 6,287,599 B1 | 9/2001 | Burnside et al. |
| 6,811,794 B2 | 11/2004 | Burnside et al. |
| 8,062,667 B2 | 11/2011 | Mehta et al. |
| 8,287,903 B2 | 10/2012 | Mehta et al. |
| 8,455,548 B2 | 6/2013 | Luhrs et al. |
| 8,557,792 B2 | 10/2013 | Castelli et al. |

OTHER PUBLICATIONS

Yale University, Guanfacine for the Treatment of Hyperactivity in Pervasive Developmental Disorder, https://clinicaltrials.gov/ct2/show/study!NCTO 1238575?term=intuniv+hyperactivity+in+au; Aug. 19, 2014.
J. Levine, et al., Inositol treatment of autism, J Neural Transm (1997) 104: 307-310.
K., Blankenship, et al., Guanfacine Extended Release in Two Patients with Pervasive Developmental Disorders, Journal of Child and Adolescent Psychopharmacology, vol. 21, No. 3, 2011, pp. 287-290.
X., Ming, et al., Use of clonidine in children with autism spectrum disorders, Brain & Development 30 (2008) 454-460.
International Search Report and Written Opinion for PCT Patent Application PCT/US2014/032933 dated Aug. 7, 2014.

*Primary Examiner* — Savitha Rao
*Assistant Examiner* — Angela Brown-Pettigrew
(74) *Attorney, Agent, or Firm* — David B. Gornish; Eckert Seamans Cherin & Mellott, LLC

(57) ABSTRACT

A method for treating a patient having ASD is disclosed. The method includes administering to the patient a therapeutically effective amount of an alpha-2 adrenergic agonist in an extended release dosage form in combination with a therapeutically effective amount of inositol.

28 Claims, No Drawings

TREATMENT OF AUTISTIC SPECTRUM DISORDER

This application is a continuation-in-part of U.S. patent application Ser. No. 14/166,483, entitled "Diagnosis and Treatment of a Form of Autistic Spectrum Disorder, filed Jan. 28, 2014, which is a continuation-in-part of U.S. patent application Ser. No. 13/860,824, entitled "Diagnosis and Treatment of P.R.I.C.E. Syndrome," filed Apr. 11, 2013, both of which are currently pending.

BACKGROUND OF THE INVENTION

1. Field of Invention

The invention relates to treatment of Autistic Spectrum Disorder. More particularly, the invention relates to administering to a person having Autistic Spectrum Disorder a therapeutically effective amount of an alpha-2 adrenergic agonist in an extended release dosage form, such as clonidine or guanfacine, preferably in combination with therapeutically effective amounts of inositol.

2. Description of Related Art

When a psychiatrist is presented with a patient exhibiting one or more behaviors such as poor social skills, defiance, lack of patience, difficulty paying attention, ritualistic behavior and/or mood swings, where such behavior(s) interferes with normal functioning, the psychiatrist must first make a diagnosis before formulating a treatment plan.

Today, the psychiatrist's nomenclature, i.e., the criteria for psychiatric evaluation and classification is provided in the Diagnostic and Statistical Manual of Mental Disorders ("DSM"), a periodically revised psychiatric "Bible" published by the American Psychiatric Association. The current version of the DSM is DSM 5.0, which was published on May 18, 2013.

The psychiatrist's professional judgment in rendering a diagnosis is largely informed by the criteria for various disorders set forth in the DSM. Thus, a psychiatrist presented with a patient exhibiting any such symptoms as those described above would consult the DSM in rendering a diagnosis. The diagnosis would, in turn, inform a treatment program. Whether a given patient is determined, for example, to have ADHD as opposed to Hypomania in Bipolar Disorder, depends on whether the patient's symptoms comport with criteria set forth for these conditions in the DSM. Proper diagnosis is critical since a wrong diagnosis will likely lead to an ineffective or even potentially harmful treatment program.

The DSM 5.0 definition of Autism Spectrum Disorder ("ASD") is as follows:

A. Persistent deficits in social communication and social interaction across contexts, not accounted for by general developmental delays, and manifest by all 3 of the following:
  1. Deficits in social-emotional reciprocity: ranging from abnormal social approach and failure of normal back and forth conversation through reduced sharing of interests, emotions, and affects and response to total lack of initiation of social interaction.
  2. Deficits in nonverbal communicative behaviors used for social interaction: ranging from poorly integrated verbal and nonverbal communication, through abnormalities in eye contact and body language, or deficits in understanding and use of nonverbal communication, to total lack of facial expression or gestures.
  3. Deficits in developing and maintaining relationships appropriate to developmental level (beyond those of caregivers); ranging from difficulties to adjusting behavior to suit different social contexts through difficulties in sharing imaginative play and in making friends to an apparent absence of interest in people.

B. Restricted, repetitive patterns of behavior, interests, or activities as manifested by at least two of the following:
  1. Stereotyped or repetitive speech, motor movements, or use of objects (such as simple motor stereotypies, echolalia, repetitive use of objects, or idiosyncratic phrases).
  2. Excessive adherence to routines, ritualized patterns of verbal or nonverbal behavior, or excessive resistance to change (such as motoric rituals, insistence on same route or food, repetitive questioning or extreme distress at small changes).
  3. Highly restricted, fixated interests that are abnormal in intensity or focus (such as strong attachment to or preoccupation with unusual objects, excessively circumscribed or perseverative interests).
  4. Hyper- or hypo-reactivity to sensory input or unusual interest in sensory aspects of environment (such as apparent indifference to pain/heat/cold, adverse response to specific sounds or textures, excessive smelling or touching of objects, fascination with lights or spinning objects).

C. Symptoms must be present in early childhood (but may not become fully manifest until social demands exceed limited capacities).

D. Symptoms together limit and impair everyday functioning.

Part A of the DSM 5.0 definition of ASD and Part B of the DSM 5.0 definition of ASD are hereinafter collectively referred to as "core symptoms" of ASD or "core ASD symptoms," since they are, by definition, present in all ASD patients. Throughout this specification, the constituent symptoms of the core symptoms of ASD may be individually referred to respectively as "part A of the DSM 5.0 definition of ASD" and "part B of the DSM 5.0 definition of ASD."

Other symptoms that may be manifest in ASD patients and which are associated with their ASD are referred to herein as "associated symptoms" of ASD or "associated ASD symptoms". Such associated symptoms of ASD may include at least one of the following: impulsivity, concentration deficit or attention deficit and emotional lability/irritability.

The term "impulsivity," as used herein, is characterized by the following: often blurts out answers before questions have been completed and/or often has difficulty waiting for his/her turn and/or often interrupts or intrudes on others (e.g., butts into conversations or games).

The terms "concentration deficit" and "attention deficit" are synonymous with each other and are therefore interchangeable. As used herein, the terms "concentration deficit" and "attention deficit" are characterized by the following: deficits in concentration as evidenced by often having difficulty sustaining attention in tasks or play activities, often does not seem to listen when spoken to directly, is often easily distracted by extraneous stimuli.

The terms "emotional lability" and "irritability," are synonymous with each other and are therefore interchangeable. As used herein, "emotional lability" and "irritability" are compounded into the single term (which is synonymous with each individual term): "emotional lability/irritability." Emotional lability/irritability is characterized by the following: severe, reactive mood swings in response to real or perceived situations where demanded needs are not being met in the environment. Emotional lability/irritability may optionally be measured using the Aberrant Behavior Checklist irritability subscale.

The DSM 5.0 provides a single broad classification called Autistic Spectrum Disorder or ASD, defined above. Patients that may have been formerly diagnosed, under the previous iteration of the DSM, with Autistic Disorder, Asperger's Disorder, Retts Disorder, Childhood Disintegrative Disorder, or PDD NOS (pervasive developmental disorder, not otherwise specified), may now be reclassified under the broad rubric of ASD. DSM 5.0 ASD defines the core symptoms that were common to these formerly recognized (under the prior iteration of the DSM) discrete pervasive developmental disorders (PDDs).

The DSM 5.0 lumps all formerly recognized discrete PDDs under the ASD umbrella because these patients all commonly share the same core symptoms of ASD, defined above. In reality, however, aside from the core symptoms, not all ASD patients are identical in terms of symptomology and treatment response. For example, drugs that are effective in treating some symptoms in the original Autistic Disorder (as defined in the prior iteration of the DSM) will not necessarily have the same effect on patients having Asperger's Disorder (as defined in the prior iteration of the DSM), even though these patients are now all lumped together as having ASD under DSM 5.0. The fact that those two previously distinct disorders are not called out in DSM 5.0 does not mean that in reality those subpopulations of ASD do not differ in terms of symptomology and treatment response (although, again, they do share the same core symptoms of ASD as defined in DSM 5.0).

The purpose of proper diagnosis is to guide proper treatment. The Applicant has discovered a pervasive subpopulation within ASD that responds particularly well to a combination therapy that the Applicant has discovered. In addition to the core symptoms of DSM 5.0 ASD, defined above, the Applicant has found patients in this subpopulation have one or more (usually all) associated symptoms of ASD, as defined above (i.e., impulsivity, concentration deficit or attention deficit and/or emotional lability/irritability). The Applicant estimates that this subpopulation makes up about 80% of ASD, and thus the vast majority of ASD patients will respond very well to this therapy, even if the specific subpopulation is not deliberately targeted. This is an especially surprising and pivotal finding, since development of effective pharmacological treatment for patients on what has been popularly referred to as the "spectrum" of autism, has confounded mental health experts and drug developers for decades.

BRIEF SUMMARY OF THE INVENTION

Accordingly, in one aspect, the present invention is directed to a method for treating a patient having ASD. As used herein, the term ASD is defined as the diagnostic criteria for DSM 5.0 as published by the American Psychiatric Association. The method includes administering to the patient a therapeutically effective amount of an alpha-2 adrenergic agonist in an extended release dosage form in combination with a therapeutically effective amount of inositol.

In another aspect, the present invention is directed to a kit including at least one first package and at least one second package. The first package contains an alpha-2 adrenergic agonist in an extended release dosage form and the second package contains inositol. The kit optionally consists essentially of at least one first package and at least one second package, wherein the first package consists essentially of an alpha-2 adrenergic agonist in an extended release dosage form and the second packet consists essentially of inositol. In this optional embodiment, no other therapeutic agent will be included that has any substantial pharmacological effect.

In another aspect, the present invention is directed to a method for reducing, to a clinically meaningful degree, one or more symptoms associated with ASD in a patient having ASD, namely, at least one of the following symptoms: (a) impulsivity; (b) concentration deficit or attention deficit and (c) emotional lability/irritability.

The method includes administering to the patient a therapeutically effective amount of an alpha-2 adrenergic agonist in an extended release dosage form and a therapeutically effective amount of inositol. A therapeutically effective amount, with respect to combination therapy, is the amount of a combination of an alpha-2-adrenergic agonist and inositol that will reduce or eliminate one or more core symptoms of ASD or associated ASD symptoms. A therapeutically effective amount of an individual therapeutic agent (an alpha-2 adrenergic agonist or inositol) is an amount of the agent that will reduce one or more core symptoms of ASD or associated ASD symptoms.

In another aspect, the present invention is directed to a therapeutic package for dispensing to, or for use in dispensing to, a patient having ASD. The therapeutic package includes one or more first unit doses and one or more second unit doses. Each one or more first unit dose includes an alpha-2 adrenergic agonist in an extended release dosage form and each one or more second unit dose includes inositol. The therapeutic package optionally consists essentially of the therapeutic agents inositol and an alpha-2-adrenergic agonist, as, in one optional embodiment, no other therapeutic agent will be included in the package that has any substantial pharmacological effect. Respective amounts of the alpha-2 adrenergic agonist and the inositol are effective, upon concomitant administration to the patient of the one or more first unit doses and the one or more second unit doses, to provide greater efficacy in reducing one or more symptoms associated with ASD than either administration of the alpha-2 adrenergic agonist in the absence of the inositol or administration of the inositol in the absence of the alpha-2 adrenergic agonist. As used herein, the phrase "greater efficacy in reducing" with respect to one or more symptoms, means that based on a psychiatrist's qualitative evaluation using ordinary skill and/or evaluation using a recognized quantitative scale in the field of ASD, optionally the Social Responsiveness Scale ("SRS," explained more fully below), the improvement in the one or more symptoms is greater, and preferably unexpectedly greater using the combination therapy, than using one pharmaceutical agent of the combination in the absence of the other. The symptoms include the core symptoms of ASD and associated symptoms of ASD as defined herein. The therapeutic package further includes a finished pharmaceutical container for containing the one or more first unit doses and the one or more second unit doses. The container further contains or includes thereon labeling directing the use of the package in the treatment of ASD.

While the present specification categorizes symptoms according to whether they are core symptoms of ASD versus associated ASD symptoms, the symptoms generally may also be categorized based on the therapeutic agents to which the Applicant has found the symptoms primarily respond in ASD patients. In this respect, the present specification may refer to a "first group of symptoms" which may include one or more of: part A of the DSM 5.0 definition of ASD, impulsivity, concentration deficit or attention deficit, and emotional lability/irritability. In another aspect, therefore, the present invention is directed to a method for reducing, to a clinically meaningful degree, one or more of a first group of symptoms in a patient having ASD. The phrase "to a clinically meaningful degree" as used herein means noticeable reduction in a given symptom based on a psychiatrist's qualitative evaluation using ordinary skill and/or evaluation using a recognized quantitative scale in the field of ASD, optionally the SRS. The method includes administering to the patient a therapeutically effective amount of an alpha-2 adrenergic agonist in an extended release dosage form. Preferably, the method further includes reducing, to a clinically meaningful degree, part B of the DSM 5.0 definition of ASD in a patient having ASD. The method includes administering, concomitantly with the therapeutically effective amount of an alpha-2 adrenergic agonist in an extended release dosage form, a therapeutically effective amount of inositol. Optionally, the alpha-2 adrenergic agonist in an extended release dosage form in combination with the therapeutically effective amount of inositol has a greater effect in reducing part A of the DSM 5.0 definition of ASD and/or the associated ASD symptom of emotional lability/irritability in the patient than either administration of the alpha-2 adrenergic agonist in the absence of the inositol or administration of the inositol in the absence of the alpha-2 adrenergic agonist.

In another aspect, the present invention is directed to a method for reducing, to a clinically meaningful degree, one or more symptoms associated with ASD in a patient having ASD. The method includes administering to the patient a maximum effective dose of inositol. The maximum effective dose of inositol is determined by providing an amount of inositol to the patient that induces diarrhea and then titrating down to a lower dose that does not induce diarrhea but is immediately below a dose which does induce diarrhea. As used herein in the foregoing context, the term "immediately below" means less than an amount which induces diarrhea, although not substantially less that amount. For example, "immediately below" may mean within 10% of the amount of inositol that induces diarrhea in the patient. The maximum effective dose according to this method is the lower dose.

In another aspect, the present invention is directed to a method for reducing, to a clinically meaningful degree, one or more symptoms associated with ASD in a patient having ASD, the method comprising administering to the patient a therapeutically effective amount of inositol, wherein the therapeutically effective amount of inositol is from about 12,000 mg to about 32,400 mg per day.

DETAILED DESCRIPTION OF THE INVENTION

The Applicant has found a heretofore unrecognized subpopulation within DSM 5.0 ASD (i.e., that by definition has the core symptoms of ASD and) that also has one or more symptoms associated with ASD, namely, at least one of the following symptoms: (a) impulsivity; (b) concentration deficit or attention deficit and (c) emotional lability/irritability.

Because this subpopulation within ASD includes one or more symptoms that mimic aspects of psychiatric disorders in non-ASD patients, psychiatrists would sometimes misdiagnose these patients and consequently misapply treatments which were of no benefit and more often exacerbated the targeted diagnosis. This phenomenon is clearly described in working examples below.

The Applicant has surprisingly discovered that ASD patients, especially within the aforementioned subpopulation, experience significant improvement in one or more core ASD symptoms and symptoms associated with ASD, through concomitant administration of extended release compositions comprising a therapeutically effective amount of an alpha-2 adrenergic agonist, such as extended release clonidine (e.g., marketed as KAPVAY®) or extended release guanfacine (e.g., marketed as INTUNIV®), with inositol (discussed further below).

Both KAPVAY® and INTUNIV® are FDA-approved for treatment of ADHD. However, Applicant has found that stimulants, which are the gold-standard for patients with true ADHD, tend to actually exacerbate symptoms in patients who have ASD, especially within this subpopulation. For those ASD patients within this subpopulation that have emotional lability/irritability, this symptom suggests a possible mood disorder, which a psychiatrist unfamiliar with this subpopulation in ASD may mistake for Bipolar Disorder, for example. A psychiatrist would be led away from prescribing KAPVAY® or INTUNIV® to patients with suspected Bipolar Disorder since it is known that alpha-2 adrenergic agonists could potentially exacerbate emotional lability/irritability found in such patients. There have been post-marketing reports in the psychiatric literature correlating the use of alpha-2 adrenergic agonists such as Tenex, INTUNIV® and KAPVAY® with the development or exacerbation of manic symptoms in Bipolar Disorder.

Extended Release Clonidine Formulations

Clonidine is an alpha-adrenergic agonist, known to be effective in various clinical disorders including hypertension; prophylaxis of common migraine headaches; subduing motor tics such as in Tourette's syndrome; and decreasing hyperactivity, impulsivity and over excitability in ADHD, and many other clinical syndromes which involve over arousal.

Clonidine is a 9-carbon, two-ringed imidazoline derivative. As used herein, the term "clonidine" denotes generally one or more of 2,6-dichloro-N-2-imidazolidinylidene benzeneamine, or benzeneamines structurally and functionally related thereto that are described in U.S. Pat. No. 3,454,701, which is incorporated herein by reference in its entirety. The term clonidine is used to include the free base of clonidine and the preferred pharmaceutically acceptable salts such as the hydrochloride, hydrobromide, sulfate, acetate, citrate and salts with other non-toxic organic and inorganic acids.

Prior to the introduction of KAPVAY® extended release clonidine, the compound clonidine had been typically given in either an oral dose in tablet form three to four times per day or via a transdermal patch. In a short-acting oral formulation, clonidine is almost completely absorbed from the gastrointestinal tract.

The primary side-effect of short-acting clonidine is sedation, particularly about an hour after the given dose when the patient may become transiently sedated, even falling asleep. There is also the problem of the drug wearing off with some rebound hyperarousal. This can occur in the middle of the night causing insomnia, and even nightmares in some cases. Such side effects have limited the practical usefulness of short-acting clonidine.

The Applicant has found short-acting dosage forms of clonidine to be ineffective in treating ASD. Extended release clonidine is capable of stable therapeutic effects by maintaining a constant serum level for an extended period in order to avoid the "peak and trough" side effects of transient sedation at peak serum levels and rebound exacerbation of symptoms at trough levels. Embodiments of extended release compositions of clonidine HCl which provide twice daily dosing are described in U.S. Pat. No. 5,869,100, which is incorporated herein by reference in its entirety.

The oral dosage units of extended release clonidine may contain one or more compositions such as diluents or fillers which are therapeutically inert and pharmaceutically acceptable and provide bulk. Examples of such diluents or fillers include cornstarch, lactulose, dextrose and the like.

The oral dosage unit of extended release clonidine can be in the form of a tablet or a capsule. Tablets may be prepared or manufactured on any conventional tableting equipment. Where the oral dosage unit is in the form of a capsule, the capsule may be, for example, any standard two-piece gelatin capsule of sufficient size for containing the formulation.

The amount of clonidine that is included per oral dosage unit may vary widely. The therapeutically effective dose range of about 0.025 mg to about 0.40 mg per unit is preferred for some applications. Twice those amounts of clonidine may be needed per oral dosage unit in a once-a-day formulation. Preferably, the therapeutically effective dose range of clonidine is about 0.0125 mg to about 0.60 mg per day, more preferably about 0.10 mg to about 0.40 mg per day. The dose of the oral dosage unit can be exactly specified, however, as required.

The cellulose ethers or mixtures thereof employed as the extended release matrix in the extended release clonidine compositions are ultra-fine, rapidly hydrating formulations having a number average molecular weight of at least 86,000 or a 2% aqueous solution of viscosity of at least 4000 cps and wherein at least 90% by weight of the cellulose ether particles can pass through a 100 mesh screen. The extended release profile of clonidine can be specified by the types or amounts of cellulose ethers used. The composition is thus very adaptable and versatile to each particular use. The oral dosage formulation herein described may provide release periods suitable for the dosing of clonidine twice per day, at twelve hour intervals. It is preferred, however, that the formulation enables once-daily dosing for treatment of ASD.

A functionally effective amount of the cellulose ether composition may be employed in the extended release clonidine formulation. Such an amount is an amount sufficient to extend the release of clonidine for up to twelve hours in some cases, and in other cases for up to about 24 hours (i.e., for once-daily dosing). Such an amount can vary and typically ranges from about 30 to about 70 weight percent, although any functionally effective amount can be employed.

A preferred extended release matrix is hydroxypropyl methylcellulose such as Methocel. A preferred Methocel has a hydroxypropoxyl substitution of from about 7 to about 12 weight percent, a methoxyl substitution of from about 28 to about 30 weight percent, a number average molecular weight of about 86,000, a 2% aqueous solution of viscosity of about 4000 cps and 95% by weight can pass through a 100 mesh screen. A preferred Methocel release period is K100M which has a hydroxypropoxyl substitution of from about 7 to about 12 weight percent, a methoxyl substitution of from about 19 to about 24 weight percent, a number average molecular weight of about 246,000, a 2% aqueous solution of viscosity of about 100,000 cps and at least 90% by weight can pass through a 100 mesh screen.

Diluents and fillers, such as cornstarch, lactulose, dextrose and the like, are included in the preparation of extended release clonidine formulation from about 30 to about 70 weight percent based on the weight of the capsule.

Extended Release Guanfacine Formulations

Guanfacine, like clonidine, is an alpha-2 adrenergic agonist, and is described in detail in U.S. Pat. No. 5,854,290, which is incorporated herein by reference in its entirety. The term guanfacine is used to include the free base of guanfacine and the preferred pharmaceutically acceptable salts such as the hydrochloride, hydrobromide, sulfate, acetate, citrate and salts with other non-toxic organic and inorganic acids. Guanfacine (N-(Aminoiminomethyl)-2,6-dichlorobenzeneacetamide; N-amidino-2-(2,6 dichlorophenyl)acetamide) in its short-acting form (Tenex) and extended release form (INTUNIV®) is an FDA approved hypotensive agent. The Applicant has found INTUNIV® to be effective in treating symptoms of ASD. Other compounds related to guanfacine that may also be effective in treating ASD include other agonists with relative selectivity for the alpha-2A subtype of adrenergic receptor, such as extended release forms of UK14304 and guanabenz, or lofexidine.

Extended released forms of guanfacine, such as the guanfacine hydrochloride, marketed as INTUNIV®, may be made, for example, according to the teachings of U.S. Pat. Nos. 6,287,599 and 6,811,794, which are incorporated herein by reference in their entireties. A therapeutically effective dose range of extended release guanfacine for treating ASD is about 0.125 mg to about 4 mg per unit, preferably about 1 mg to about 4 mg per unit.

One extended release guanfacine tablet formulation comprises, in addition of course to the active agent guanfacine (e.g., as a hydrochloride), at least one non-pH dependent sustained release agent, and at least one pH-dependent agent that increases the rate of release of the guanfacine from the tablet at a pH in excess of 5.5, such as at least one organic acid that maintains an acidic micro-environment in the tablet. A similar tablet may include clonidine in place of guanfacine as the active agent. In general, the pharmaceutically active agent is present in the composition in an amount of from about 0.1 wt, % to about 70 wt. %, preferably from about 1 wt. % to about 40 wt %.

Non-pH-dependent sustained release agents which may be included in the composition include, but are not limited to, ethylcellulose, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, and stearyl alcohol. In general, the at least one non-pH-dependent sustained release agent is present in the composition in an amount of from about 5 wt. % to about 50 wt. %, preferably from about 10 wt. % to about 30 wt. %. It is to be understood, however, that the scope of the present invention is not to be limited to any particular non-pH-dependent sustained release agents.

pH-dependent agents that increase the rate of release of the at least one pharmaceutically active agent from the tablet at a pH in excess of 5.5 include, but are not limited to, polymers that swell at a pH in excess of 5.5, and enteric agents, and/or agents that increase the solubility of the at least one pharmaceutically active agent at a pH greater than 5.5, by maintaining an acidic microenvironment in the tablet, e.g., an organic acid. The at least one pH-dependent agent is present in the composition in an amount of from about 0.5 wt. % to about 40 wt. %, preferably from about 1 wt. % to about 20 wt. %.

Polymers that swell at a pH in excess of 5.5 include, but are not limited to, acrylic acid copolymers, sodium alginate, carrageenan, alginic acid, pectin, and sodium carboxymethyl cellulose.

Enteric agents include, but are not limited to, cellulose acetate phthalate, hydroxypropyl methylcellulose phthalate, polyvinyl acetate phthalate, methacrylic acid copolymers, cellulose acetate trimellitate, hydroxypropyl methylcellulose acetate, succinate, shellac, and zein.

Agents that increase the solubility of the at least one pharmaceutically active agent at a pH greater than 5.5 include, but are not limited to, organic acids. Such organic acids maintain an acidic microenvironment in the tablet, and include, but are not limited to, citric acid, fumaric acid, tartaric acid, adipic acid, glucono delta-lactone, and malic acid.

The composition of the present invention may further include other materials such as bulking agents, disintegrating agents, anti-adherants and glidants, lubricants, and binding agents.

Bulking agents include, but are not limited to, microcrystalline cellulose (e.g., Avicel®, FMC Corp., Emcocel®, Mendell Inc.), mannitol, xylitol, dicalcium phosphate (e.g., Emcompress, Mendell Inc.) calcium sulfate (e.g., Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.). The bulking agent may be present in the composition in an amount of from about 5 wt. % to about 90 wt. %, preferably from about 10 wt. % to about 50 wt. %.

Disintegrating agents which may be included in the composition include, but are not limited to, microcrystalline cellulose, starches, crospovidone (e.g., Polyplasdone XL, International Specialty Products.), sodium starch glycolate (Explotab, Mendell Inc.), and crosscarmellose sodium (e.g., Ac-Di-Sol, FMC Corp.). The disintegrating agent may be present in the composition in an amount of from about 0.5 wt. % to about 30 wt %, preferably from about 1 wt. % to about 15 wt. %.

Antiadherants and glidants which may be employed in the composition include, but are not limited to, talc, corn starch, silicon dioxide, sodium lauryl sulfate, and metallic stearates. The antiadherant or glidant may be present in the composition in an amount of from about 0.2 wt. % to about 15 wt. %, preferably from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil (sterotex), talc, and waxes, including but not limited to, beeswax, carnuba wax, cetyl alcohol, glyceryl stearate, glyceryl palmitate, glyceryl behenate, hydrogenated vegetable oils, and stearyl alcohol. The lubricant may be present in an amount of from about 0.2 wt. % to about 20 wt. %, preferably from about 0.5 wt. % to about 5 wt. %.

Binding agents which may be employed include, but are not limited to, polyvinyl pyrrollidone, starch, methylcellulose, hydroxypropyl methylcellulose, carboxymethyl cellulose, sucrose solution, dextrose solution, acacia, tragacanth and locust bean gum. The binding agent may be present in the composition in an amount of from about 0.2 wt. % to about 10 wt. %, preferably from about 0.5 wt. % to about 5 wt. %.

The compositions of the present invention may be made, for example, by a direct compression method, or by a wet granulation method. In the direct compression method, the pharmaceutically active agent and other ingredients are sieved through a stainless steel screen, such as a 40 mesh steel screen. The sieved materials then are charged to a suitable blender, and blended for 10 minutes with an intensifier bar on for 3 minutes. The blend then is compressed into tablets on a rotary press using appropriate tooling. The compressed tablets may be coated, if desired.

In the wet granulation method, the pharmaceutically active agent and other ingredients are granulated with a granulating fluid (e.g., isopropyl alcohol, ethyl alcohol, and water) in a planetary mixer, high shear mixer, or fluidized bed granulator. Binding agents may be contained in the granulating fluid, or may be in the dry mix. The wet granules are dried in an oven or fluidized bed dryer, and then sieved through a suitable screen to obtain free flowing granules. The resulting granules were blended with a suitable lubricant and glidant, and the lubricated granules are compressed into tablets on a rotary press using appropriate tooling. If desired, a coating can be applied onto the compressed tablets.

Alpha-2 Adrenergic Agonists and Salts Thereof

The term "alpha-2 adrenergic agonist" is used herein to include the free base thereof and the preferred pharmaceutically acceptable salts such as the hydrochloride, hydrobromide, sulfate, acetate, citrate and salts with other non-toxic organic and inorganic acids.

Alternative Alpha-2 Adrenergic Agonists

Alternative alpha-2 adrenergic agonists are disclosed in U.S. Pat. No. 8,455,548, which is incorporated by reference herein in its entirety. Examples of agents disclosed in that patent include compounds having the following structures:

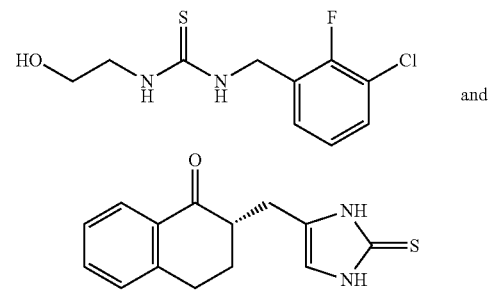

and

It is contemplated that therapeutically effective amounts of alpha-2 adrenergic agonists disclosed in U.S. Pat. No. 8,455,548 may be used according to some embodiments of the present invention.

Liquid and Other Alternative Formulations of Clonidine or Guanfacine

Alternatively, extended release clonidine or guanfacine for the treatment of a psychiatric disorder, for example ASD, and/or one or more symptoms associated with ASD, may be administered orally as a liquid formulation. It is preferred that such a liquid formulation is tasteless and/or odorless because children who have ASD are very particular, do not like swallowing pills and do not respond favorably to medications with strong tastes or smells. It is also preferred that such a liquid formulation is therapeutically effective for treating ASD with once-a-day administration. Extended release liquid formulations may be prepared, for example, according to the teachings of U.S. Pat. Nos. 8,062,667 and 8,287,903, both of which are incorporated herein by reference. Those two patents purportedly cover Quillivant XR, a recently approved extended release liquid form of Ritalin (methylphenidate hydrochloride) for treatment of ADHD.

Alternatively, extended release clonidine or guanfacine for the treatment of ASD and/or one or more symptoms associated with ASD, may be administered in the form of a transdermal patch, a nasal spray, an inhalation mist, a rectal suppository, an injection or a powder. If the dosage form is a powder, it may be mixed into a beverage, combined with food (e.g. apple sauce) or reconstituted (e.g. by a pharmacist) into a liquid oral formulation.

Combination Therapy Using Inositol and Clonidine or Guanfacine

In another aspect, the present invention contemplates a combination therapy for treatment of ASD and/or one or more symptoms associated with ASD. Such combination therapy would include a therapeutically effective amount of an alpha-2 adrenergic agonist (e.g., clonidine or guanfacine) in extended release dosage form in combination with a therapeutically effective amount of inositol. The inositol may be concomitantly administered with therapeutic doses of extended release clonidine or extended release guanfacine, as needed. The term "concomitantly administered" and "concomitant administration," as used herein with respect to two or more pharmaceutical agents, means that the agents are given in close enough temporal proximity to allow their individual therapeutic effects to overlap. Thus, concomitant administration may include providing the two or more agents in a single formulation, in separate formulations administered simultaneously or in separate administrations given minutes within each other or longer (for example, a once-daily therapeutically effective amount of an alpha-2 adrenergic agonist in extended release dosage form that is given to a patient in the morning, is "concomitantly administered" with inositol given once in the morning and once at night since the therapeutic effects of the once-daily alpha-2 adrenergic agonist last all day). For example, combination therapy according to one aspect of the present invention may optionally be in the form of a single extended release formulation comprising inositol and clonidine or guanfacine in, e.g., solid or liquid oral dosage forms. However, it is contemplated that separate but concomitant administration of the alpha-2 adrenergic agonist in an extended release dosage form and inositol is preferable to a combined dosage form comprising fixed amounts of both agents, because separate dosage administration would allow physicians to dose-titrate each agent as appropriate for a given patient.

Inositol or cyclohexane-1,2,3,4,5,6-hexyl is a chemical compound with formula $C_6H_{12}O_6$ or $(-CHOH-)_6$, a six-fold alcohol (polyol) of cyclohexane. Inositol exists in nine possible stereoisomers. The most prominent form, widely occurring in nature, is cis-1,2,3,5-trans-4,6-cyclohexanehexyl, or myo-inositol (former name meso-inositol). Inositol has been shown to have a taste that is half the sweetness of table sugar. For this reason, the Applicant has found the taste of inositol to be well tolerated by ASD patients who are very particular and who thus do not respond favorably to medications with strong tastes or smells.

The isomer myo-inositol—again the most prominent form of naturally occurring inositol—is a meso compound which has an optically inactive plane of symmetry through the molecule. Besides myo-inositol, the other naturally occurring (albeit uncommon) stereoisomers are scyllo-, muco-, D-chiro-, and neo-inositol. Other isomers are L-chiro-, allo-, epi-, and cis-inositol.

The structure of the most common natural form of inositol, myo-inositol, is shown below:

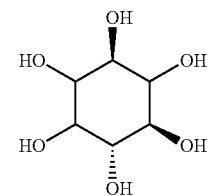 [SMILES: OC1C(O)[C@H](O)[C@@H](O)C(O)[C@H]1O]

A preferred form of inositol for use according to some embodiments of the present invention is myo-inositol sold in powder form under the name FREEDA®. Unless otherwise stated in this specification, the term "inositol" or "standard inositol" refers to myo-inositol having a potency substantially similar to that of the inositol powder referenced above, e.g., sold under the name FREEDA®, or other brands and dosage forms having substantially similar potencies. Therapeutically effective doses of inositol (e.g., in powder form) for patients with ASD may generally range from about 4,500 mg to about 32,400 mg per day and preferably from about 9,000 mg to about 32,400 mg per day and especially preferably from about 12,000 mg to about 32,400 mg per day, or optionally from about 12,000 mg to about 24,000 mg per day, or optionally from about 12,000 to about 18,000 mg per day. Once daily administration of inositol within the foregoing dosage amounts is within the scope of the invention. However, twice daily or three times daily administration is preferred. For example, if a preferred daily dose of inositol for a given patient is 21,000 mg, it is preferred that the inositol be administered to the patient, e.g., 10,500 mg in the morning and 10,500 mg in the evening (twice daily dosing) or 7,000 in the morning, 7,000 around lunch time and 7,000 in the evening (three times daily dosing). For a minority of patients, especially in an adult ASD population (over age 18), therapeutically effective doses of inositol may be less than 4,500 mg/day to as low as about 500 mg/day.

In treating ASD patients with inositol, the Applicant has discovered, among other things, the following noteworthy phenomena:
  (1) Inositol may be safely administered, with only the minimal side effect of diarrhea, in doses that significantly exceed doses given to non-ASD patients described in the literature.
  (2) By and large, children (i.e., under age 18) as a population tend to tolerate higher doses of inositol than adults as a population, in terms of the side-effect of diarrhea. For example, as a population, children tend to respond well to about 9,000 mg or more of inositol twice a day, whereas adults tend to tolerate (but at the same time, only require) about half as much. A minority of patients, especially in the adult population, experience diarrhea with much lower doses of inositol. For example, the Applicant has treated patients for whom about 500 mg per day was the maximum dose that would avoid diarrhea, yet that dose was still therapeutically effective in those patients.

(3) The Applicant has found a correlation between the maximum effective dose of inositol in an ASD patient and the point at which the inositol induces diarrhea in the patient. In other words, once a patient experiences diarrhea from inositol, the point of diminishing returns has been reached, as it appears to the Applicant that increasing the inositol dose at that point will not further reduce ASD symptoms to a clinically meaningful degree. While the Applicant would not recommend deliberately inducing diarrhea in a patient for ethical reasons, it is believed that the maximum effective dose of inositol for a given patient is immediately below an amount that induces diarrhea in the patient. The preferred therapeutically effective dose of inositol is the maximum effective dose, although the present invention may include doses of inositol that are therapeutically effective and below the maximum effective dose. While it is not practical to dose titrate ASD patients on inositol by altering the hundreds or more likely thousands of milligram doses of inositol one milligram at a time, one may alter the dose by tens or more likely hundreds of milligrams at a time to determine the maximum effective dose of inositol. For example, in one aspect of the present invention, the maximum effective dose of inositol for a given patient is determined by providing an amount of inositol to the patient that induces diarrhea and then titrating down to a lower dose that does not induce diarrhea but is immediately below a dose which does induce diarrhea, wherein the maximum effective dose is the lower dose. A physician may titrate down, e.g., in increments of 5% or 10% of the amount of inositol that induces diarrhea in the patient. Optionally, the maximum effective dose is within 10% of the amount of inositol that induces diarrhea in the patient. In such an embodiment, for example, the maximum effective dose for a patient who experienced diarrhea at 18,000 mg of inositol per day may be immediately below 18,000 mg, including as low as 16,200 mg.

While it is currently preferred that the inositol is administered within the nominal dosage ranges described above, it is contemplated that the potency of inositol may be increased such that it may be administered in lesser nominal amounts than described above with reference to standard inositol, but still provide therapeutically equivalent effectiveness within the scope of the present invention. For example, the Applicant contemplates that inositol could be effectively administered in two to three times lower doses than the nominal amounts described above according to the teachings of U.S. Pat. No. 8,557,792, the entirety of which is incorporated herein by reference. That patent discloses a vitamin B12 formulation and inositol is considered to be part of the vitamin B complex.

If taken in powder form, inositol is typically dissolved in food or drink. It is contemplated that the inositol can also be administered in solid oral dosage forms too, such as in tablets or capsules.

Alternatively, as mentioned above, therapeutically effective amounts of inositol and clonidine or guanfacine may be combined in a single oral formulation. In one aspect, this formulation may be in a solid oral dosage form, such as in a tablet or capsule. It is also contemplated that this oral formulation may be in a liquid formulation—preferably one that is tasteless and odorless. The oral formulation may be used for twice daily administration, but more preferably once daily administration.

As described in examples below, it has been found that inositol nicely complements KAPVAY® or INTUNIV® in more effectively treating core ASD symptoms and symptoms associated with ASD in patients having ASD, than either inositol or the extended release alpha-2 adrenergic agonist alone. In particular, the Applicant has found that the combination of inositol with KAPVAY® or INTUNIV® directly addresses core symptoms of ASD. Further, the Applicant has found that inositol complements the alpha-2 adrenergic agonist's treatment of the associated ASD symptom of emotional lability/irritability, in ASD patients exhibiting that symptom. In the Applicant's estimation, addition of inositol helps ASD sufferers (especially children) to be less overly focused on socially irrelevant preoccupations (i.e., ameliorates part B of the DSM 5.0 definition of ASD) and to be less emotionally aroused (i.e., ameliorates emotional lability/irritability associated with ASD). At the same time the applicant has found that, KAPVAY® or INTUNIV® help ASD sufferers (especially children), among other things, to be more focused on relevant stimuli (i.e., ameliorates the associated ASD symptom of concentration deficit or attention deficit) and to be less impulsive (i.e., ameliorates the associated ASD symptom of impulsivity). The unexpected combined effects of inositol with an extended release alpha-2 adrenergic agonist are actually marked improvement in part A of the DSM 5.0 definition of ASD and the associated ASD symptom of emotional lability/irritability, through a synergy of the two agents, to a degree that use of either agent alone would not suggest. As used herein, "synergy" is used to describe an improvement in the behavior of an ASD patient that is achieved by the combined use of an extended release alpha-2-adrenergic agonist and inositol as compared to the use of either the extended release alpha-2-adrenergic agonist alone or inositol alone in an ASD patient.

Thus, the invention, in one aspect, is a therapy for a psychiatric disorder such as ASD comprising, in combination, a therapeutically effective amount of an alpha-2 adrenergic agonist in an extended release dosage form and a therapeutically effective amount of inositol. The invention, in another aspect, is a method of treating a patient having a psychiatric disorder such as ASD comprising administering to the patient, in combination, a therapeutically effective amount of an alpha-2 adrenergic agonist in an extended release dosage form and a therapeutically effective amount of inositol.

The invention, in another aspect is directed to a method for reducing, to a clinically meaningful degree, one or more core symptoms of ASD and/or symptoms associated with ASD in a patient having ASD. The method includes administering to the patient a therapeutically effective amount of an alpha-2 adrenergic agonist in an extended release dosage form and a therapeutically effective amount of inositol. The symptoms to be reduced according to this method include one or more of: part A of the DSM 5.0 definition of ASD, part B of the DSM 5.0 definition of ASD, impulsivity, concentration deficit or attention deficit and emotional lability/irritability. Preferably the combination of the agents reduces at least one of the foregoing symptoms to a greater extent than either agent alone. More preferably this greater extent is at least additive, even more preferably, in some embodiments, more than additive.

It is contemplated that the alpha-2 adrenergic agonist and inositol, either in a combined dosage form or separate dosage forms, may be in the form of a solid oral dosage form (e.g., tablet, capsule, disintegrating tablet, gummy or lozenge), a liquid oral dosage form, a transdermal patch, a nasal spray, an inhalation mist, a rectal suppository, an injection or a powder. If the dosage form is a powder, it may be mixed into a beverage, combined with food (e.g. apple sauce) or reconstituted (e.g. by a pharmacist) into a liquid oral formulation. It is further contemplated that combination therapy according to the invention may use an alpha-2 adrenergic agonist in one dosage form and inositol in another dosage form, or both the same dosage form, either in a single combined dosage form or separately.

Kits and Therapeutic Packages for Treating ASD

In one aspect, the present invention is directed to a kit comprising or optionally consisting essentially of at least one first package and at least one second package, the first package containing or optionally consisting essentially of an alpha-2 adrenergic agonist (e.g., clonidine or guanfacine, in any of the dosage forms described above) in an extended release dosage form, the second package containing or optionally consisting essentially of inositol (in any of the dosage forms described above). In an optional embodiment wherein the kit consists essentially of at least one first package and at least one second package, and the first package consists essentially of an alpha-2 adrenergic agonist in an extended release dosage form and the second package consists essentially of inositol, no other therapeutic agent will be included in the package that has any substantial pharmacological effect. Optionally, the kit would include instructions to co-administer contents of the first package with contents of the second package to a patient having ASD. Preferably, the kit includes a plurality of second packages, for example 30 to 120 second packages, optionally 45 to 120 second packages, optionally 60 to 120 second packages, optionally 75 to 120 second packages, optionally 90 to 120 second packages. Optionally, each second package contains from about 4,500 mg to about 9,000 mg inositol. Optionally, if the alpha-2 adrenergic agonist is a solid oral dosage form of clonidine, the dosage form comprises 0.1 mg of clonidine or 0.2 mg of clonidine. Optionally, if the alpha-2 adrenergic agonist is a solid oral dosage form of guanfacine, the dosage form comprises 1 mg of guanfacine, or 2 mg of guanfacine, or 3 mg of guanfacine or 4 mg of guanfacine.

In another aspect, the present invention is directed to a therapeutic package for dispensing to, or for use in dispensing to, a patient having ASD. The therapeutic package includes one or more first unit doses and one or more second unit doses. Each one or more first unit dose includes an alpha-2 adrenergic agonist (e.g., clonidine or guanfacine) in an extended release dosage form and each one or more second unit dose includes inositol. Respective amounts of the alpha-2 adrenergic agonist and the inositol are effective, upon concomitant administration to the patient of the one or more first unit doses and the one or more second unit doses, to provide greater efficacy in reducing part A of the DSM 5.0 definition of ASD and/or the associated ASD symptom of emotional lability/irritability, than either administration of the alpha-2 adrenergic agonist in the absence of the inositol or administration of the inositol in the absence of the alpha-2 adrenergic agonist. The therapeutic package further includes a finished pharmaceutical container for containing the one or more first unit doses and the one or more second unit doses. The container further contains or includes thereon labeling directing the use of the package in the treatment of ASD. Optionally, the greater efficacy in reducing the aforementioned symptom(s) is at least additive or greater than additive.

Measurement of ASD Symptoms

It is within the ability of a psychiatrist of ordinary skill to assess each of the various symptoms and diagnostic criteria for ASD generally and for other symptoms associated with ASD described herein, in a clinical setting, using his or her training and experience. Optionally, a psychiatrist may desire to measure these symptoms and criteria using a recognized quantitative scale in the field of ASD, optionally the Social Responsiveness Scale ("SRS"). The Social Responsiveness Scale (SRS) (Constantino, J. et al., J Dev Behav Pediatr, 21:2-11 (2000); Constantino, J. et al., J Autism Dev Disord., 3:427-433 (2003)) is a norm-referenced, 65-item report questionnaire developed to measure social behaviors, including social awareness, social information processing, reciprocal social communication, and social anxiety, in both clinical and non-clinical populations. It is designed for use with children ages 4 through 18. The SRS items measure ASD symptoms in the domains of social awareness, social information processing, reciprocal social communication, social anxiety/avoidance, and stereotypic behavior/restricted interests. Each item is scored from 1 (not true) to 4 (almost always true). Scores are obtained for five treatment subscales: Social Awareness (e.g., "Is aware of what others are thinking or feeling"), Social Cognition (e.g., "Doesn't recognize when others are trying to take advantage of him or her"), Social Communication (e.g., "Avoids eye contact or has unusual eye contact"), Social Motivation (e.g., "Would rather be alone than with others"), and Autistic Mannerisms (e.g., "Has an unusually narrow range of interests").

Examples of Treatment for ASD Patients

Aspects of the present invention are further explained by the following examples which should not be construed by way of limiting the scope of the present invention.

Example 1

A patient was initially diagnosed ten years ago with alleged Attention Deficit Hyperactivity Disorder (ADHD) at age six by his original psychiatrist due to difficulties with concentration and impulsivity which impaired his social and academic functioning, following normal labs and physical examination. The patient's mother's pregnancy and delivery were unremarkable. The patient met normal developmental, motor milestones. The patient was tried on many psychostimulant medications, which are the gold standard for treatment of ADHD. Medications in this class include: Adderall/XR, Focalin/XR, Dexedrine, Vyvanse, Ritalin/LA/ER, Metadate ER/CD, Concerta and Daytrana. Despite adequate dosing and duration of trials of several such psychostimulants, the patient manifested an increase in agitation and impulsivity without improving concentration in school on these medications, instead of the calming effect stimulant medication is expected to exert in ADHD patients.

After the failure of these psychostimulants to improve the patient's symptoms, the psychiatrist separately tried Strattera, Wellbutrin, Provigil and Nuvigil to treat ADHD, all of which similarly increased agitation and impulsivity in this patient. In addition, many of these medications produced the typical side effects of decreased appetite, abdominal pain, nausea and difficulty sleeping at night. These side effects limited the drugs' usefulness, particularly in these patients who are particular, rigid and inflexible when it comes to accepting change—in this case, the side effects themselves.

Next, the psychiatrist attempted to address the patient's impulsivity with three-times-daily, short-acting guanfacine (Tenex), followed by short-acting clonidine, followed by propranolol, which were not effective because they were too sedative. Also, the thrice-daily dosing of these drugs left peaks and troughs in the patient's symptoms and difficulty with compliance during the school day.

Due to a failure of ADHD treatments, the psychiatrist concluded that this patient did not have ADHD. The psychiatrist thus changed his treatment approach to address alleged Obsessive Compulsive Disorder (OCD) symptoms that the patient manifested, such as rigidity and preoccupation with his daily routine which often distracted the patient and caused him to become impulsive and irritated when he did not get his way. He was tried on many serotonergic medications (selective serotonin re-uptake inhibitors ("SSRI's") and serotonin and norepinephrine reuptake inhibitors ("SNRIs"), which are the gold standard for treatment of OCD. Medications in this class include Celexa, Lexapro, Prozac, Luvox/CR, Paxil/CR, Zoloft, Pristiq, Effexor/XR, Cymbalta and Remeron. Despite adequate dosing and duration of trials of several of these SSRI/SNRI medications, the patient manifested an increase in agitation and impulsivity without improvement in concentration in school on these medications, instead of the calming effect SSRI/SNRI medications were expected to exert in OCD patients.

The psychiatrist next presumed that the activation of agitation and impulsivity in the patient on psychostimulants and serotonergic medications suggested an underlying mood disorder such as pediatric Bipolar. In addition, the psychiatrist determined that the observed impulsivity must represent a pediatric manifestation of hypomania, despite the absence of other hypomanic symptoms found in the then-current version of the DSM. By convention, psychiatrists refer to this phenomenon as Bipolar III or hypomania induced by medication which predicts and unmasks the development of spontaneous mood swings of genuine Bipolar to come for the patient later in life.

With the patient diagnosed (or rather, misdiagnosed) as having pediatric Bipolar, the psychiatrist tried a series of mood stabilizers to address the patient's impulsivity, such as Lithium, Depakote, Topamax, Trileptal, Tegretol, and Lamictal—all of which proved ineffective and resulted in the side effects of worsening the patient's concentration. Given the lack of efficacy of the mood stabilizers and the lack of clear evidence for Bipolar Disorder in this patient, the psychiatrist turned his attention to a possible Pervasive Developmental Disorder such as Asperger's Disorder, since the patient never exhibited the speech delay required to qualify for a diagnosis of Autistic Disorder (which prior to DSM 5.0 was recognized as a distinct disorder from Asperger's and other PDDs, but is now conflated with these previously distinct disorders under DSM 5.0 ASD, as explained above). Yet this patient did not meet all criteria for Asperger's Disorder either, except that he lacked normal social skills. Nevertheless, the psychiatrist tried a series of atypical antipsychotics, including Zyprexa, Geodon, Seroquel as well as two FDA approved drugs for treatment of irritability in Autistic Disorder, Abilify and Risperdal. These medications caused the patient severe sedation, impaired his concentration further and caused an increase in both appetite and weight. These side effects caused the patient further irritation.

After this series of misdiagnoses and treatment regimens that exacerbated the patient's condition, the patient was sixteen years old when he first met with the Applicant for a psychiatric evaluation. The Applicant determined that the patient was worse on his then-current medication regimen than he was without it. He had been taking Daytrana, which appeared to worsen his agitation without helping his concentration. He had been taking Lexapro which also appeared to be worsening his agitation without helping his rigidity. He had been taking Depakote and Lamictal which was making him tired, was not helping his agitation and impaired his concentration. His diagnosis was completely unclear until the Applicant evaluated him for the diagnostic criteria for the subpopulation Applicant discovered in ASD, which in addition to the core symptoms of ASD, includes one or more of the following associated ASD symptoms: impulsivity, concentration deficit or attention deficit and emotional lability/irritability. It was found that the patient met the core criteria for ASD and in addition, exhibited every one of the aforementioned symptoms associated with ASD.

The Applicant tapered and discontinued the aforementioned medications in the patient. The Applicant then titrated up KAPVAY® as follows: 0.1 mg at bedtime for a week; next, 0.1 mg twice a day for a week; next, 0.1 mg in the morning and 0.2 mg at night for one week; and finally 0.2 mg twice a day going forward. Symptoms in this patient were dramatically improved without side effects. The patient still had mild, residual particular tendencies of rigidity with rules and schedule for which the Applicant added Inositol powder (sold under the name FREEDA®) 2 and ½ teaspoons (9000 mg) twice a day, which was well tolerated. Within one month, the patient appeared as a normal teenager. He went off his medications while on vacation and all of his symptoms returned. He then resumed his regimen and became normal again. Thus, a patient who had been misdiagnosed and consequently suffered for so many years, was finally able to live as basically a normal teenager because he was given the appropriate therapy which the Applicant discovered is effective for treating such patients.

Example 2

The Applicant evaluated a sixteen year old patient who had a history of the core symptoms of ASD and also (what the Applicant now recognizes as) symptoms associated with ASD, including impulsivity, concentration deficit or attention deficit and emotional lability/irritability. As discussed below, the clinical significance of this symptomology had not been previously appreciated or diagnosed by this patient's psychiatrists prior to the patient's evaluation by Applicant.

The patient had been misdiagnosed as having OCD four years ago and was given Prozac and Zoloft. These drugs did not alleviate the restricted areas of interest, repetitive behavior and caused the patient to become "wild" and unable to sleep. Risperdal was added to the patient's therapeutic regimen for mood swings associated with possible Bipolar Disorder, misdiagnosed due to the activation on the SSRI's and to help control agitation associated with possible Asperger's Disorder. However, the patient did not meet criteria for Asperger's Disorder other than lacking social skills. Risperdal was then discontinued due to sedation and weight gain. The patient was switched to Abilify which also caused sedation and tremor without improvement in concentration.

By the time the patient met with the Applicant for an initial psychiatric evaluation, he was worse on his then-current medication regimen than he was without it. He had been taking Zoloft and Abilify, as well as Melatonin to help him sleep. His diagnosis was completely unclear until the Applicant evaluated him for core symptoms of ASD and associated ASD symptoms including impulsivity, concentration deficit or attention deficit and emotional lability/irritability.

The Applicant tapered and discontinued the patient's then-current medications. The Applicant then titrated up INTUNIV® 1 mg at bedtime, increasing by an additional 1 mg at bedtime every week as necessary to achieve symptom control, up to a maximum of 4 mg.

This patient ultimately did very well on INTUNIV® 2 mg at bedtime, which also helped him sleep at night. The addition of Inositol 9000 mg twice a day for "getting stuck" on certain topics in conversation was found to be therapeutically beneficial. On this new treatment, the core symptoms of ASD and associated ASD symptoms in this patient were dramatically improved without side effects. It was found that when this patient went off his medications, e.g., on holidays, all core symptoms of ASD and associated ASD symptoms returned. When he resumed his treatment regimen, he was normal again.

Example 3

A six year old patient, who happens to be the Applicant's son, has the core symptoms of ASD as well as symptoms associated with ASD, including impulsivity, concentration deficit or attention deficit and emotional lability/irritability. This patient had been evaluated by other specialists, who had determined that he had some type of pervasive developmental disorder (PDD-NOS), for which there was no known treatment. This patient's condition rendered him unfit to be in a mainstream school with children who have normal social skills.

The Applicant initiated treatment using 1 mg of INTUNIV® once per day and Inositol 9000 mg twice a day. The results were nothing short of miraculous. All core symptoms of ASD (parts A and B of the DSM 5.0 definition of ASD) and symptoms associated with ASD (impulsivity, concentration deficit or attention deficit and emotional lability/irritability), were significantly improved and without side effects. The Applicant, as both a psychiatrist and father who lives with this patient can attest to the effectiveness and tolerability of this treatment. The Applicant noted that his son would completely relapse when off drug but become "normal" again upon resuming treatment. For example, the patient's symptoms returned when the INTUNIV® and inositol was withheld on weekends, but would abate upon resuming administration of the drug during the school week.

If the Applicant had simply accepted that his son had some form of PDD-NOS, the Applicant could have accepted the conventional wisdom that there is no treatment for his son. Alternatively, the Applicant could have tried to treat certain symptoms of his son's using medications that were known for conditions that some of those symptoms suggested, such as ADHD, OCD and Bipolar Disorder. But such attempts would have yielded no beneficial results or, more likely, would have had adverse effects. This is precisely what happened to the patients described in Examples 1 and 2 above, before the Applicant diagnosed them with ASD and developed an appropriate therapy for them.

INTUNIV® and inositol has made the difference for the Applicant's son between the need for expensive tax payer or private resources exceeding $50,000 a year in special education services and a normal, mainstream, elementary school education, which is to the patient's maximal benefit. He is now immersed in a classroom of children with normal social skills and is thriving in that environment.

Example 4

The Applicant conducted a retrospective study of medical charts of the Applicant's ASD patients who, in addition to having the core symptoms of ASD, also had symptoms associated with ASD (impulsivity, concentration deficit or attention deficit and emotional lability/irritability). 175 of these patients had initially received some form of medication (not treatment according to the present invention) or had been given psychotherapy without medication. Of these, 22% responded in some way to the medication and 17% responded in some way to psychotherapy alone. 77% of those on one or more of the following medications experienced adverse effects: stimulants, SSRI's, SNRI's, mood stabilizers, antipsychotics, benzodiazepines and immediate release alpha-2 agonists.

The retrospective study also considered the following four groups of ASD patients who, in addition to having the core symptoms of ASD, had associated ASD symptoms of impulsivity, concentration deficit or attention deficit and emotional lability/irritability. Patients in these groups were administered some form of treatment according to aspects of the present invention:

Group 1—Patients who were given inositol alone;
Group 2—Patients who were given extended release guanfacine HCl alone;
Group 3—Patients who were given extended release clonidine HCl alone; and
Group 4—Patients who were given extended release guanfacine HCl or extended release clonidine HCl, in combination with inositol.

Group 1 included 66 patients, 62 of which (94%) showed improvement in part B of the DSM 5.0 definition of ASD and the associated ASD symptom of emotional lability/irritability. 12% of Group 1 patients experienced a minimal side effect of diarrhea, which was substantially resolved with dosage reduction.

Group 2 included 88 patients, 84 of which (95%) showed improvement in part A of the DSM 5.0 definition of ASD and associated ASD symptoms of impulsivity, concentration deficit or attention deficit and emotional lability/irritability, with a minimal side effect of sedation (6%).

Group 3 included 25 patients, 22 of which (88%) showed improvement in part A of the DSM 5.0 definition of ASD and associated ASD symptoms of impulsivity, concentration deficit or attention deficit and emotional lability/irritability, with a minimal side effect of sedation (20%).

Group 4 included 34 patients, 33 of which (97%) showed improvement of all core symptoms of ASD and associated symptoms of ASD, without increased incidence of adverse effects found in any group alone.

Particularly noteworthy from this retrospective study is the extent to which an alpha-2 adrenergic agonist in an extended release dosage form in combination with inositol improved part A of the DSM 5.0 definition of ASD in the study patients. In isolating data gathered on part A of the DSM 5.0 definition of ASD in patients in Groups 1, 2, 3 and 4 described above, the following was observed. Only 2 out of 66 (3% of) patients in Group 1 showed improvement in part A of the DSM 5.0 definition of ASD through administration of inositol alone. 65 out of 88 (74% of) patients in Group 2 showed improvement in part A of the DSM 5.0 definition of ASD through administration of extended release guanfacine alone. 17 out of 25 (68% of) patients in Group 3 showed improvement in part A of the DSM 5.0 definition of ASD through administration of extended release clonidine alone. Surprisingly, 33 out of 34 (97% of) patients in Group 4 showed marked improvement in part A of the DSM 5.0 definition of ASD through administration of extended release guanfacine or extended release clonidine in combination with inositol.

Example 5

Comparative Study of Four Treatment Groups of ASD Patients

A study is conducted involving 28 patients who qualify for an ASD diagnosis. In a first phase, these patients are divided into two groups: a drug group (16 patients) that receives therapeutic amounts of inositol (average from 9,000 mg to 18,000 mg per day) in an oral powder dosage form for two weeks; and a placebo group (12 patients) that receives a confectionary sugar-based powdered placebo (intended to represent inositol) for two weeks. Neither group receives any other psychiatric drug during the two weeks of drug or placebo administration. After those two weeks, the progress of the patients in the two groups are measured according to the SRS. It is found that all 16 patients in the drug (inositol alone) group show clinically meaningful reduction in the restricted areas of interest and repetitive behaviors subscale of the SRS. However, none of the 12 patients in the placebo group show any measurable reduction in the restricted areas of interest and repetitive behaviors subscale of the SRS.

In a second phase of the study, the 28 patients are divided into the following four groups:

Group 1—4 patients are given placebos representing inositol and placebos representing INTUNIV®;

Group 2—8 patients are given real inositol and placebos representing INTUNIV®;

Group 3—8 patients who receive real inositol in the first phase of the study continue to receive the inositol and, in addition, are given real INTUNIV®. The INTUNIV® is titrated up from a daily dose of 1 mg to 2 mg, 3 mg or 4 mg as needed for a given patient; and Group 4—8 patients are given placebos representing inositol and are given real INTUNIV®. The INTUNIV® is titrated up from a daily dose of 1 mg to 2 mg, 3 mg or 4 mg as needed for a given patient.

The results after 8 weeks of the second phase of this study are as follows. Group 1 patients show no measurable improvement in SRS total score or any SRS subscales compared to their condition prior to the second phase of the study. Group 2 patients show clinically meaningful improvement as measured by the restricted areas of interest and repetitive behaviors subscale of the SRS, which in turn improves the patients' overall SRS score. Group 3 patients show clinically meaningful improvement as measured by the SRS, both in terms of total SRS score and according to SRS subscales. Group 4 patients show clinically meaningful improvement as measured by the total SRS score, but not in the restricted areas of interest and repetitive behaviors subscale of the SRS.

In sum, the results show that ASD patients who receive therapeutically effective amounts of an alpha-2 adrenergic agonist in an extended release dosage form in combination with a therapeutically effective amount of inositol experience greater improvement in total SRS score than ASD patients receiving one agent in the absence of the other.

Example 6

Open Label Study Using Combination Therapy on ASD Patients

In a third phase of the study described in Example 5, the 28 patients from Example 5 are all placed on the combination treatment regimen of the patients of Group 3 (i.e., therapeutically effective amounts of real inositol in combination with therapeutically effective amounts of real INTUNIV®). This third phase is an open label study phase which lasts eight weeks. At the conclusion of the third phase, it is found that 27 out of the 28 patients show clinically meaningful improvement in total SRS score and according to each SRS subscale. This example demonstrates the effectiveness of combination therapy for ASD patients according to an aspect of the present invention, compared to mono therapy using one agent in the absence of the other in this patient population.

Example 7

Open Label Study in which Treatment for ASD Patients is Incrementally Withdrawn

In an open label fourth phase of the study described in Example 6, all 28 patients that had received combination therapy are taken off inositol. After two weeks off inositol, these patients' scores on the restricted areas of interest and repetitive behaviors subscale of the SRS return to pre-inositol levels. Next, the INTUNIV® is titrated down, eventually to zero, for all 28 patients. After two weeks completely off the INTUNIV®, the SRS total scores of the patients revert to pre-study (i.e, untreated ASD) levels.

There is an urgent public health need for the mental health community to understand that a significant percentage of ASD patients respond exceptionally well with minimal side effects to inositol in combination with INTUNIV® or KAPVAY®. The Applicant's invention provides a readily available, safe and comparatively low-cost means to enable these ASD sufferers to lead normal lives. Widespread implementation of this invention would substantially address the exorbitant educational, medical and societal costs caused by this condition.

While the invention has been described in detail and with reference to specific examples thereof, it will be apparent to one skilled in the art that various changes and modifications can be made therein without departing from the spirit and scope thereof.

What is claimed is:

1. A method for treating a patient having core symptoms of Autism Spectrum Disorder ("ASD") comprising administering to the patient a therapeutically effective amount of an alpha-2 adrenergic agonist in an extended release dosage form in combination with a therapeutically effective amount of inositol, wherein the therapeutically effective amount of inositol is from about 9,000 mg to about 32,400 mg per day and wherein the method treats the patient's core symptoms of ASD.

2. The method of claim 1, wherein the patient has core symptoms of ASD and at least one associated ASD symptom selected from the group consisting of: impulsivity, concentration deficit or attention deficit and emotional lability/irritability.

3. The method of claim 1, wherein the patient has associated ASD symptom of emotional lability/irritability, the therapeutically effective amount of an alpha-2 adrenergic agonist in an extended release dosage form in combination with the therapeutically effective amount of inositol being effective to reduce the emotional lability/irritability.

4. The method of claim 1, wherein the therapeutically effective amount of an alpha-2 adrenergic agonist in an extended release dosage form in combination with the therapeutically effective amount of inositol has a greater effect in addressing part A of the DSM 5.0 definition of ASD in the patient than either administration of the alpha-2 adrenergic agonist in the absence of the inositol or administration of the inositol in the absence of the alpha-2 adrenergic agonist.

5. The method of claim 4, wherein the greater effect is at least additive.

6. The method of claim 4, wherein the greater effect is greater than additive.

7. The method of claim 4, wherein the greater effect is measured according to the Social Responsiveness Scale.

8. The method of claim 1, wherein the alpha-2 adrenergic agonist is selected from the group consisting of clonidine and guanfacine.

9. The method of claim 1, wherein the therapeutically effective amount of inositol is from about 12,000 mg to about 32,400 mg per day.

10. The method of claim 1, wherein the therapeutically effective amount of inositol for a patient is a maximum effective dose for the patient, the maximum effective dose being immediately below an amount that induces diarrhea in the patient.

11. The method of claim 10, wherein the maximum effective dose is within 10% of the amount of inositol that induces diarrhea in the patient.

12. The method of claim 1, wherein the therapeutically effective amount of inositol is given in twice daily administrations.

13. The method of claim 1, wherein the therapeutically effective amount of inositol is given in three times daily administrations.

14. The method of claim 1, wherein the alpha-2 adrenergic agonist is clonidine and the therapeutically effective amount of clonidine is from about 0.0125 mg to about 0.60 mg per day.

15. The method of claim 14, wherein the therapeutically effective amount of clonidine is from about 0.10 mg to about 0.60 mg per day.

16. The method of claim 1, wherein the alpha-2 adrenergic agonist is guanfacine and the therapeutically effective amount of guanfacine is from about 0.125 mg to about 4 mg per day.

17. The method of claim 1, wherein the alpha-2 adrenergic agonist is in a dosage form selected from the group consisting of: a solid oral dosage form, liquid oral dosage form, and a transdermal patch; and wherein the inositol is in a dosage form selected from the group consisting of: tablets, capsules, powder, and a liquid oral dosage form.

18. A method for reducing at least one core Autism Spectrum Disorder ("ASD") symptom and at least one associated ASD symptom in a patient having ASD, the method comprising administering to the patient a therapeutically effective amount of an alpha-2 adrenergic agonist in an extended release dosage form and a therapeutically effective amount of inositol, wherein the therapeutically effective amount of inositol is from about 9,000 mg to about 32,400 mg per day and wherein the method treats the patient's at least one core ASD symptom and the patient's at least one associated ASD symptom.

19. The method of claim 18, wherein the at least one core ASD symptom is selected from the group consisting of: part A of the DSM 5.0 definition of ASD and part B of the DSM 5.0 definition of ASD, and wherein the at least one associated ASD symptom is selected from the group consisting of: impulsivity, concentration deficit or attention deficit, and emotional lability/irritability.

20. The method of claim 18, wherein the alpha-2 adrenergic agonist is selected from the group consisting of clonidine and guanfacine.

21. The method of claim 18, wherein the therapeutically effective amount of inositol is from about 12,000 mg to about 32,400 mg per day.

22. The method of claim 18, wherein the therapeutically effective amount of inositol for a patient is a maximum effective dose for the patient, the maximum effective dose being immediately below an amount that induces diarrhea in the patient.

23. The method of claim 22, wherein the maximum effective dose is within 10% of the amount of inositol that induces diarrhea in the patient.

24. The method of claim 18, wherein the therapeutically effective amount of inositol is given in twice daily administrations.

25. The method of claim 18, wherein the therapeutically effective amount of inositol is given in three times daily administrations.

26. The method of claim 18, wherein the therapeutically effective amount of an alpha-2 adrenergic agonist in extended release dosage form in combination with the therapeutically effective amount of inositol has a greater effect in reducing the at least one core ASD symptom and/or the at least one associated ASD symptom in the patient than either administration of the alpha-2 adrenergic agonist in the absence of the inositol or administration of the inositol in the absence of the alpha-2 adrenergic agonist.

27. The method of claim 26, wherein the greater effect is at least additive.

28. The method of claim 26, wherein the greater effect is greater than additive.

* * * * *